United States Patent [19]

Lahr et al.

[11] Patent Number: 5,368,864
[45] Date of Patent: Nov. 29, 1994

[54] FORMULATION OF OXYPURINOL AND/OR ITS ALKALI AND ALKALINE EARTH SALTS

[75] Inventors: Wolfgang Lahr; Guido Weickgenannt, both of Berlin, Germany

[73] Assignee: Henning Berlin GmbH Chemie- und Pharmawerk, Berlin, Germany

[21] Appl. No.: 37,684

[22] Filed: Mar. 25, 1993

Related U.S. Application Data

[63] Continuation of Ser. No. 688,497, Jul. 19, 1991, abandoned.

[30] Foreign Application Priority Data

Nov. 25, 1988 [DE] Germany ............... 3839825

[51] Int. Cl.$^5$ ................................. A61K 9/14
[52] U.S. Cl. ........................... 424/489; 514/257
[58] Field of Search .................. 424/489; 514/257

[56] References Cited

U.S. PATENT DOCUMENTS 4,978,668 12/1990 Babbs ........................... 514/258
5,021,242  6/1991 Römer ........................... 424/489

FOREIGN PATENT DOCUMENTS 2546371  4/1977 Germany .
 975850 11/1964 United Kingdom .
2187954  9/1987 United Kingdom .

OTHER PUBLICATIONS

Chemical Abstracts, vol. 83, No. 2, 14 Jul. 1975 (Columbus, Ohio, US), J. H. Collett et al.; "Effects of polyvinylpyrrolidone on the solubility and dissolution rate of allopurinol", see p. 340, abstract 15544t, & J. Pharm. Pharmacol. 1974, 26, Suppl., 84P–85P.

Journal of Pharmaceutical Sciences, vol. 60, No. 9, Sep. 1971, Win Loung Chiou et al.: "Pharmaceutical applications of solid dispersion systems", pp. 1281–1302.

*Primary Examiner*—Thurman K. Page
*Assistant Examiner*—Raj Bawa
*Attorney, Agent, or Firm*—Wegner, Cantor, Mueller & Player

[57] ABSTRACT

Formulations of oxypurinol and/or its alkali or alkaline earth salts in non-crystalline form, containing the active substance in the form of a solids dispersion with pharmacologically harmless adjuvants. They have more rapid and higher solubility than oxypurinol and/or its alkali or alkaline earth salts. They can be used for the preparation of drugs having high bioavailability of the active substance oxypurinol.

10 Claims, No Drawings

FORMULATION OF OXYPURINOL AND/OR ITS ALKALI AND ALKALINE EARTH SALTS

This application is a continuation of U.S. patent application Ser. No. 07/688,497 filed Jul. 19, 1991, now abandoned.

Oxypurinol (4,6-dihydroxypyrazolo[3,4-d]pyrimidine) represents the active major metabolite of allopurinol known in therapy of gout. Oxypurinol is sparingly soluble in water and digestive juice, and therefore, due to associated insufficient absorbability, practically did not find entry in therapy.

It is known from German Offenlegungsschrift DE-OS 37 07 999 to use oxypurinol for reducing cell damage, namely in form of an injectable form of administration. Oral application of these preparations according to prior art is not mentioned and is not practicable due to pH values of up to 12 prevalent with these forms, because burns are to be expected upon oral administration.

Alkali and alkaline earth salts of oxypurinol have improved solubility as compared to the acid. For instance, aqueous solutions of oxypurinol sodium monohydrate have a pH value of 9.5 and permit concentrations of about 1.5% at 25° C. However, such pH values are non-physiological.

Under physiological conditions, i.e., at pH values of about from 1.0 to 7.5, as prevalent in the human digestive tract, solubility still is insufficient. Particularly, the rate of dissolution of oxypurinol and its salts is low. Thus, the solubility of oxypurinol sodium monohydrate in 0.1N hydrochloric acid, which corresponds approximately to the acidity of an empty stomach, was determined as being 43 mg/l after 5 minutes (about 0.004%) and 142 mg/l (about 0.014%) after 60 minutes, respectively.

As used in the sense of the present invention, rate of dissolution is understood to be the mass of substance, which is dissolved within a certain time period. Solubility, on the other hand, is understood to be the mass of substance having dissolved clearly in a mass or a certain volume of solvent.

Solubility and rate of dissolution of a drug substance are rate-determining for its afflux in the systemic circulation and thus for the degree of bioavailability.

Thus, it is an object of the invention to improve solubility and rate of dissolution of oxypurinol.

This problem can be solved in a surprisingly simple manner by formulations of oxypurinol and/or its alkali or alkaline earth salts in non-crystalline form, characterized in that they contain the active substance in the form of a dispersion of solids with pharmacologically harmless adjuvants in a ratio of from 1:0.2 to 1:10, preferably in a ratio of from 1:1 to 1:4.

Formulations are obtained, characterized in that oxypurinol contained therein has a rate of dissolution of more than 100 mg/l per 5 minutes at a pH value of between 1.0 and 7.5.

Particularly preferred are formulations, characterized in that the terminal solubility of oxypurinol contained therein is the saturation concentration and is maintained for longer than one hour.

These formulations may contain additional active substances or may be admixed with these, if desired.

The preparation of the formulations according to the invention is carried out in that oxypurinol and/or its alkali or alkaline earth salts are dissolved together with said adjuvants, optionally with addition of solvent, or are dissolved in an adjuvant melt, and the melts or solutions obtained are cooled and/or dried.

As solvent, use of water is preferred.

In principle, all adjuvants are possible as pharmacologically harmless adjuvants that can either be molten or dissolved by a solvent, such adjuvants being preferred, in the melts or solutions of which oxypurinol and/or its alkali or alkaline earth salts can be dissolved in considerable amounts as well. When such melts or solutions are cooled down rapidly and/or dried, dispersions of solids or so-called "solid solutions" are formed, wherein oxypurinol and/or its alkali or alkaline earth salts are present in non-crystalline form.

The preparation of the formulations according to the invention is carried out, for instance, in that the active substance and the adjuvants are molten together and are cooled down by casting into plates, dropping upon cooled supports into beads, pouring into pulled-out blister cups, or spray solidification. Also, these melts may optionally be dosed directly into capsules.

By adding a solvent, the preparation is effected especially simply and mildly. In principle, all readily removable organic solvents and solvent mixtures such as alcohols and alcohol/water mixtures are to be considered. Especially preferred ecologically and economically is water as solvent.

The preparation of the solutions can be carried out, for instance, in that the active substance is first pre-dissolved in the solvent, and then a solution of adjuvants is admixed. It is also possible to incorporate the active substance into an adjuvant solution afterwards. Removal of solvent is subsequently effected by volatilization, evaporation in vacuo, by spray drying or freeze drying.

Preferred adjuvants for the preparation of the solid dispersions are polyethylene glycols having average molecular weights of from 200 to about 35,000, polyvinylpyrrolidone (e.g., Kollidon, 17, 25, 30, 90), polyvinyl acetate, heteropolymerizates from Polyvinylpyrrolidone/polyvinyl acetate (e.g., Kollidon, VA 64), polyvinyl alcohols of most varied degrees of saponification, cellulose derivatives such as sodium carboxymethylcellulose, hydroxyethylcellulose, hydroxypropylmethylcellulose, acrylic acid derivatives such as polyacrylic acid (e.g., Carbopol,), the adjuvants being used alone or as mixtures. Particularly preferred adjuvants are polyethylene glycols and polyvinylpyrrolidones. Optionally, surfactants or wetting agents are added. The ratio of oxypurinol or one of its salts to adjuvants used is from 1:0.2 to 1:10, ratios of more than 1:0.8 being particularly preferred, especially, where a solid dispersion free of residual crystalline proportions is to be obtained. Thus, particularly preferred are ratios of from 1:1 to 1:4 to prepare drug forms making administration more feasible with respect to mass or size, since large drug forms, in particular, do not ensure the desired patient compliance. The dried or solidified solid dispersions may either be divided directly in correct doses for oral administration, for example, in the form of capsules, or may be pressed into tablets together with further adjuvants such as fillers, agents enhancing disintegration, wetting agents and lubricants. Optionally, such tablets are provided with a coating of, for instance, acrylic acid or cellulose derivatives, to which pigments and dyes may be admixed. If, with high dosage, large drug forms are prepared that might impede administration as, for instance, tablets, then these are provided with one or more scores, so that fragments of the drug form or partial doses can be administered.

Of course, solid dispersions of oxypurinol and/or its alkali or alkaline earth salts may be processed with additional active substances to give combination preparations, for instance, with benzbromarone. Furthermore, drug forms may be prepared in which oxypurinol is preferably contained in form of a mixture of solid dispersion and crystalline active substance.

Another possibility for preparing solid dispersions from oxypurinol or its salts is to add to the previously described solutions or melts, prior to drying or solidification, further adjuvants, which, for instance, improve tableting properties of the solid dispersion, or enhance disintegration rate of the drug form. Such adjuvants are those that make no or little contribution to the formation of a solids dispersion, such as, for example, microcrystalline cellulose, cross-linked polyvinylpyrrolidone, lactose, starch, etc. After removal of the solvent or after solidification, a mixture of the dispersion with these adjuvants is obtained, which can be processed by known methods to the drug forms mentioned.

Solid dispersions of the kind described previously or drug forms prepared therefrom rapidly liberate the active substance on contact with natural or artificial digestive juices in a pH range of about from 1.0 to 7.5, i.e., values of pH ranges predominant in the human digestive tract. In particular, the rate of dissolution of oxypurinol or one of its salts in the strongly acidic region, namely at pH values of about from 1.0 to 2.0, i.e., conditions as being met in an empty stomach, is increased by several times when compared to the pure active substances, that amount of dissolved active substance being deemed as measure for the rate of dissolution, that is present in dissolved form after 5 minutes residence time in the test medium.

The solubility of a solid substance under standardized conditions is a constant for the substance. For oxypurinol sodium monohydrate, it was found, for example, that maximum solubility after 24 hours is about 280 mg/l solvent, and is gradually decreasing after another 24 hours. Thus, the solubility of oxypurinol sodium monohydrate as a constant for the substance can be determined to be about 260 mg/l. Besides increased rate of dissolution of the formulations according to the invention, there is also increased solubility, giving rise to supersaturated solutions. Therefore, it was surprising to observe that with the formulations according to the invention, an increased "terminal solubility" results, being maintained for at least several hours, to decrease only then to the solution's degree of saturation of the solution corresponding to solubility as a constant for the substance.

Due to increased rate of dissolution and increased "terminal solubility" of oxypurinol or its salts, the active substance can be absorbed rapidly and to a high degree. Correspondingly, it has good bioavailability. Thus, the formulations according to the invention are very well suited to be used in drugs for the treatment of hyperuricaemia and gout.

In the following examples, the formulations according to the invention, their preparation and their use are discussed in greater detail.

Example 1

| | |
|---|---|
| Oxypurinol sodium monohydrate | 6.0 g |
| Polyethylene glycol (average molecular weight 6,000) | 18.0 g |
| Polyvinylpyrrolidone (Kollidon ®, 25) | 6.0 g |
| Distilled water | 96.0 g |

Polyethylene glycol and Kollidon ®, are pre-dissolved in water. The oxypurinol salt is dissolved with warming. The solution being virtually clear is evaporated to dryness in vacuo.

Glassy products are obtained, containing no crystals according to microscopic evaluation.

Example 2

| | |
|---|---|
| Oxypurinol sodium monohydrate | 2.0 g |
| Polyvinyl alcohol (Mowiol ®, type 8.88) | 2.0 g |
| Polyethylene glycol (average molecular weight 6,000) | 1.0 g |
| Distilled water | 40.0 g |

Polyvinyl alcohol, polyethylene glycol, and oxypurinol salt are successively dissolved in water with warming. After evaporation of water in vacuo, a glassy product is formed, being virtually free of crystals.

Example 3

| | |
|---|---|
| Oxypurinol sodium monohydrate | 1.0 g |
| Distilled water | 30.0 g |
| Polyvinylpyrrolidone/Polyvinyl acetate heteropolymerizate (Kollidon ®, VA 64) | 1.0 g |
| Polyethylene glycol (average molecular weight 6,000) | 1.0 g |

Oxypurinol is dissolved in water with warming. After addition of Kollidon ®, and polyethylene glycol, the clear solution is evaporated to dryness.

Example 4

| | |
|---|---|
| Oxypurinol sodium monohydrate | 5.0 g |
| Distilled water | 250.0 g |
| Polyvinylpyrrolidone/Polyvinyl acetate heteropolymerizate (Kollidon ®, VA 64) | 2.5 g |
| Polyethylene glycol (average molecular weight 10,000) | 2.5 g |

Oxypurinol is dissolved in water with warming. After addition of Kollidon ®, and polyethylene glycol, the clear solution is dried in a spray drier in a hot air stream at about 150° C.

Example 5

| | |
|---|---|
| Oxypurinol (free acid) | 5.0 g |
| Distilled water | 100.0 g |
| Polyvinylpyrrolidone/Polyvinyl acetate heteropolymerizate (Kollidon ®, VA 64) | 1.0 g |
| Polyethylene glycol (average molecular weight 6,000) | 1.0 g |

Oxypurinol is dissolved in water at 95° C. After addition of Kollidon ®, and polyethylene glycol, evaporation to dryness is effected in vacuo.

Example 6

| | |
|---|---|
| Oxypurinol sodium monohydrate | 0.5 g |
| Distilled water | 50.0 g |
| Hydroxypropylcellulose | 2.0 g |

Oxypurinol is dissolved in water at 80° C. The cellulose is suspended in the solution and cooled with stirring. The clear solution is evaporated to dryness in vacuo.

Example 7

| | |
|---|---|
| Oxypurinol sodium monohydrate | 10.0 g |
| Distilled water | 50.0 g |
| Polyvinylpyrrolidone/Polyvinyl acetate heteropolymerizate (Kollidon ®, VA 64) | 5.0 g |
| Polyethylene glycol (average molecular weight 10,000) | 5.0 g |
| Microcrystalline cellulose (Avicel ®, PH 102) | 20.0 g |

Oxypurinol is dissolved in water at 70° C. After addition of Kollidon ®, and polyethylene glycol, microcrystalline cellulose is stirred into the clear solution. The suspension is evaporated to dryness in vacuo.

Example 8

| | |
|---|---|
| Oxypurinol sodium monohydrate | 5.0 g |
| Distilled water | 250.0 g |
| Polyvinylpyrrolidone/Polyvinyl acetate heteropolymerizate (Kollidon ®, VA 64) | 2.5 g |
| Polyethylene glycol (average molecular weight 10,000) | 2.5 g |

The preparation of the solids dispersion is carried out analogously to example 3.

Example 9

| | |
|---|---|
| Solids dispersion | 3.00 g |
| Cross-linked polyvinylpyrrolidone (Polyplasdone ®, XL) | 1.50 g |
| Stearic acid | 0.06 g |
| Highly dispersed silicic acid (Aerosil ®, 200) | 0.09 g |
| | 4.65 g |

The dispersion of solids containing oxypurinol was mixed with the adjuvants indicated, and pressed to give tablets having a content of 150 mg of active substance. Two tablets, corresponding to 300 mg of oxypurinol sodium monohydrate, were tested for liberation of active substance.

The forms according to the invention were tested for solubility and rate of dissolution, respectively, in comparison to crystalline oxypurinol sodium monohydrate finely powdered in a mortar.

| Test Model | |
|---|---|
| Dissolution tester: | United States Pharmacopoeia (USP XXI) |
| Test medium: | 0.1 N hydrochloric acid |
| Test volume: | 1,000 ml |
| Test temperature: | 37° C. |
| Rotary speed: | 90 rpm |

Measurements were effected spectrophotometrically at 245 nm. The measurement results are shown in the following table 1.

TABLE 1

Dissolved amount of active substance in mg/liter (cumulated values) from:

| | Reference | Ex. 1 Test 1 | Ex. 1 Test 2 | Ex. 1 Test 3 | Ex. 4 | Ex. 7 | Ex. 8 |
|---|---|---|---|---|---|---|---|
| 5 min | 43 | 228 | 434 | 360 | 350 | 357 | 255 |
| 10 min | 62 | 245 | 429 | 380 | 384 | 388 | 267 |
| 20 min | 88 | 262 | — | — | 417 | 409 | 278 |
| 30 min | 115 | 266 | 406 | 377 | 413 | 411 | 285 |
| 45 min | 126 | — | 384 | — | 402 | 409 | 285 |
| 60 min | 142 | 270 | — | 381 | 407 | 411 | 289 |
| 180 min | 207 | — | 340 | 374 | 404 | 393 | 287 |
| 24 hrs | 280 | 276 | 246 | — | — | — | — |
| 48 hrs | 263 | — | — | — | — | — | — |

The formulations according to the invention thus liberate the active substance contained therein more rapidly already after a measurement time of 5 minutes, as compared to the reference, so that the rate of dissolution typically can be increased from about 43 mg/5 min to about 430 mg/5 min. Correspondingly high is the terminal solubility, since the active substance does not recrystallize at once, but is available for absorption in a sufficiently long time in dissolved state during its residence time in the stomach and in the upper digestive tract.

Moreover, the results from table 2 are proving that the formulations according to the invention have a solubility superior to that of the crystalline form in the claimed pH value range of about from 1.0 to 7.5 as well.

TABLE 2

Solubility according to example 1 (test 3) as a function of pH value and time as compared to crystalline active substance (values in mg/liter)

| | pH = 1.5 | | pH = 3.0 | | pH = 4.5 | | pH = 6.5 | |
|---|---|---|---|---|---|---|---|---|
| Time | cryst. | solids dispersion | cryst. | solids dispersion | cryst. | solids dispersion | cryst. | solids dispersion |
| 5 minutes | 43 | 360 | 81 | 382 | 85 | 435 | 243 | 502 |
| 10 minutes | 62 | 380 | 110 | 402 | 110 | 431 | 261 | 528 |
| 60 minutes | 143 | 381 | 222 | 398 | 243 | 423 | 290 | 562 |

We claim:

1. Formulation of oxypurinol or its alkali or alkaline earth salt in non-crystalline form, wherein the oxypurinol or its salt is contained in the form of a solids dispersion with pharmacologically inert adjuvants in a ratio of from 1:0.2 to 1:10.

2. A formulation according to claim 1, wherein the ratio of oxypurinol or its salt to adjuvants is from 1:1 to 1:4.

3. A formulation according to claim 1, wherein oxypurinol contained therein has a rate of dissolution of more than 100 mg/l per 5 minutes at a pH range of between 1.0 and 7.5.

4. A formulation according to claim 1, which contains additional active substances.

5. A process for the preparation of a formulation of oxypurinol or its alkali or alkaline earth salts in non-crystalline form, wherein the oxypurinol or its salt and pharmacologically inert adjuvants, at a ratio of 1:0.2 to 1:10, are dissolved together in a solvent or melted together, and then cooled and/or dried, avoiding crystallization.

6. The process as claimed in claim 5, wherein the ratio of oxypurinol or its salt to adjuvants is 1:1 to 1:4.

7. The process as claimed in claim 5, wherein water is used as a solvent.

8. A method of treating hyperuricaemia and gout, comprising administering to a patient in need thereof a formulation according to claim 1.

9. A formulation according to claim 1, wherein the non-crystalline form of oxypurinol maintains a solubility greater than its constant saturation concentration for more than one hour.

10. A formulation according to claim 2, wherein the non-crystalline form of oxypurinol maintains a solubility greater than its constant saturation concentration for more than one hour.

* * * * *